(12) United States Patent
Chang

(10) Patent No.: US 7,687,647 B2
(45) Date of Patent: Mar. 30, 2010

(54) PROPYLENE OXIDE PROCESS

(75) Inventor: Te Chang, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 28 days.

(21) Appl. No.: 12/157,110

(22) Filed: Jun. 6, 2008

(65) Prior Publication Data

US 2009/0306416 A1    Dec. 10, 2009

(51) Int. Cl.
*C07D 301/06* (2006.01)

(52) U.S. Cl. ..................... 549/532; 549/533

(58) Field of Classification Search ............... 549/532, 549/533
See application file for complete search history.

(56) References Cited

U.S. PATENT DOCUMENTS

| | | | |
|---|---|---|---|
| 4,954,325 A | 9/1990 | Rubin et al. | |
| 5,973,171 A | 10/1999 | Cochran et al. | |
| 6,077,498 A | 6/2000 | Diaz Cabañas et al. | |
| 6,114,551 A | 9/2000 | Levin et al. | |
| 6,498,259 B1 | 12/2002 | Grey et al. | |
| 7,138,535 B1 | 11/2006 | Whitman et al. | |

FOREIGN PATENT DOCUMENTS

BE    1001038 A7    6/1989

OTHER PUBLICATIONS

R. Szostak, "Non-aluminosilicate molecular sieves," in Molecular sieves: Principles of synthesis and identification (1989), p. 205, Van Nostrand Reinhold.

G. Vayssilov, "Structural and physicochemical features of titanium silicalites", in Catal. Rev.-Sci. Eng., (1997). p. 209, vol. 39(3).

T. Maschmeyer et al., "Heterogeneous catalysts obtained by grafting metallocene complexes onto mesoporous silica", in Nature, (Nov. 1995), p. 159, vol. 378 (9).

P. T. Tanev et al., "Titanium-containing mesoporous molecular sieves for catalytic oxidation of aromatic compounds", in Nature, (Mar. 1994), p. 321, vol. 368.

A. Corma et al., J. Chem.Soc., Chem. Commun., (1998), p. 579.

D. Wei et al., "Catalytic behavior of vanadium substituted mesoporous molecular sieves", in Catal. Today, (1999), pp. 501, vol. 51.

R. H. Perry et al., "Evaporators" in Perry's chemical engineers' handbook, Seventh edition, (1997), pp. 11/107-114, McGraw Hill.

*Primary Examiner*—Bernard Dentz
*Assistant Examiner*—David E Gallis
(74) *Attorney, Agent, or Firm*—Yuanzhang Han

(57) ABSTRACT

A process for making propylene oxide from propylene is disclosed. The process comprises reacting propylene, oxygen, and hydrogen in the presence of a catalyst, a solvent, and a buffer to produce a reaction mixture comprising propylene oxide. Separation of light components from the reaction mixture gives a heavy residue comprising the buffer. The buffer is precipitated from the heavy residue by a precipitating agent.

14 Claims, 1 Drawing Sheet

PROPYLENE OXIDE PROCESS

FIELD OF THE INVENTION

The invention relates to a process for producing propylene oxide by reacting propylene, oxygen, and hydrogen in the presence of a catalyst, a solvent, and a buffer.

BACKGROUND OF THE INVENTION

Propylene oxide is an important industrial chemical intermediate. Propylene oxide can be produced by direct oxidation of propylene with oxygen and hydrogen in a solvent in the presence of a catalyst (U.S. Pat. Nos. 7,138,535 and 5,973,171). A buffer helps to improve the selectivity to propylene oxide (U.S. Pat. No. 6,498,259).

The copending application Ser. No. 11/588,453, filed Oct. 27, 2006, teaches an improved process for producing epoxide by catalytic reaction of olefin, hydrogen, and oxygen wherein the reaction is modified by the presence of buffer salts in the reaction mixture. The improvement comprises recovering the buffer by electrodialysis and/or crystallization and recycling the recovered buffer to the reaction.

SUMMARY OF THE INVENTION

The invention is a process for making propylene oxide from propylene, oxygen, and hydrogen. The process comprises reacting propylene, oxygen, and hydrogen in the presence of a catalyst, a solvent, and a buffer to produce a reaction mixture comprising propylene oxide and buffer. Separation of light components from the reaction mixture gives a heavy residue comprising the buffer. The buffer is precipitated from the heavy residue by a precipitating agent.

DETAILED DESCRIPTION OF THE INVENTION

Figure 1:
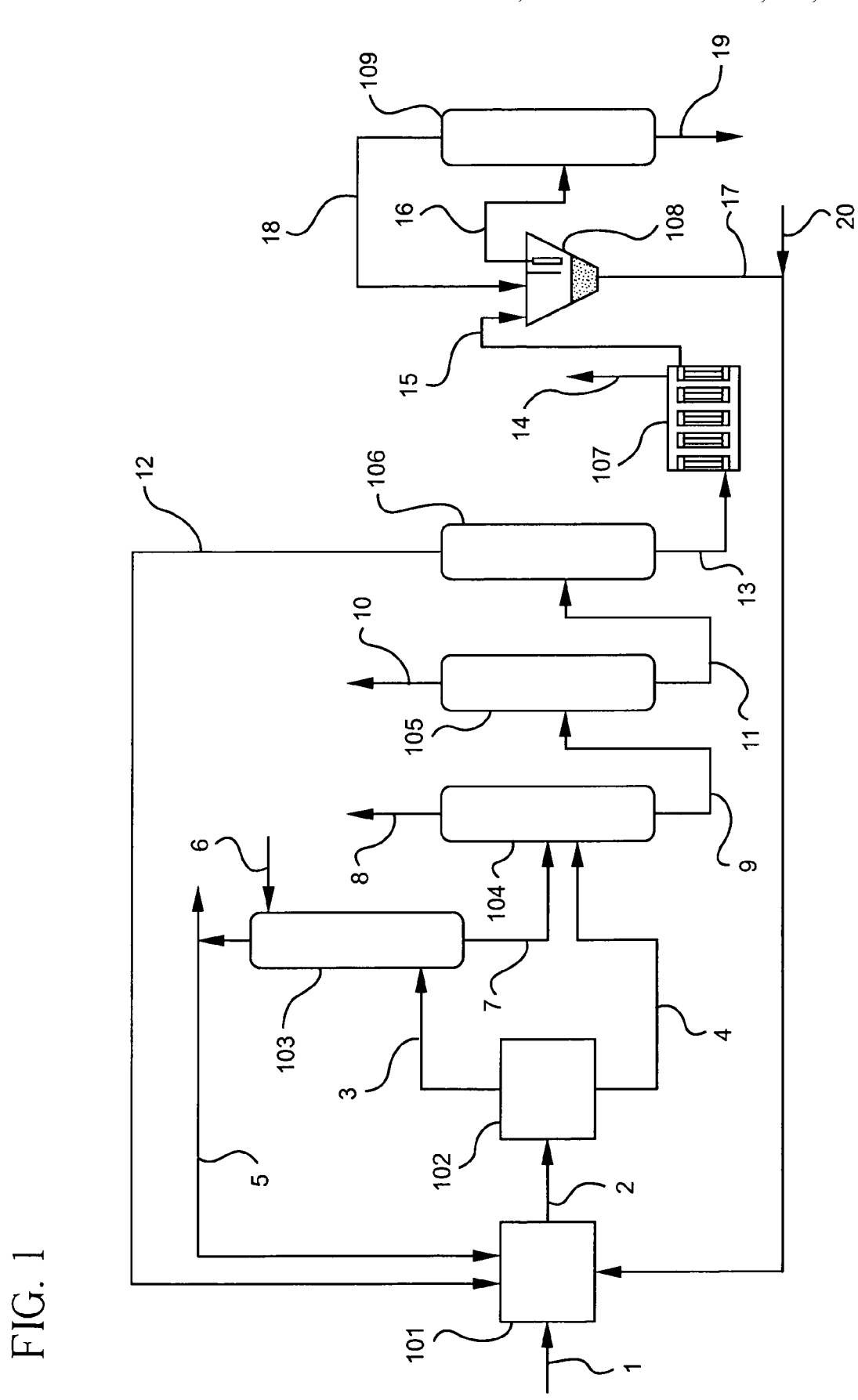
FIG. 1 is a schematic presentation of one embodiment of the present invention.

The process comprises reacting propylene, oxygen, and hydrogen in the presence of a catalyst ("the reaction step"). A suitable catalyst comprises a transition metal zeolite and a noble metal. Zeolites generally contain one or more of Si, Ge, Al, B, P, or the like, in addition to oxygen. A transition metal zeolite (e.g., titanium zeolite, vanadium zeolite) is a crystalline material having a porous molecular sieve structure and containing a transition metal. A transition metal is a Group 3-12 element. The first row of these includes elements from Sc to Zn. Preferred transition metals are Ti, V, Mn, Fe, Co, Cr, Zr, Nb, Mo, and W. Particularly preferred are Ti, V, Mo, and W. Most preferred is Ti. Titanium silicalite-1 (TS-1, a titanium silicalite having an MFI topology analogous to that of the ZSM-5 aluminosilicate) is particularly preferred.

Suitable titanium zeolites include titanium silicates (titanosilicates). Preferably, they contain no element other than titanium, silicon, and oxygen in the lattice framework (see R. Szostak, "Non-aluminosilicate Molecular Sieves," in *Molecular Sieves: Principles of Synthesis and Identification* (1989), Van Nostrand Reinhold, pp. 205-282). Small amounts of impurities, e.g., boron, iron, aluminum, phosphorous, copper, and mixtures thereof, may be present in the lattice. The amount of impurities is preferably less than 0.5 weight percent (wt %), more preferably less than 0.1 wt %. Preferred titanium silicates will generally have a composition corresponding to the following empirical formula: $xTiO_2 \cdot (1-x)SiO_2$, where x is between 0.0001 and 0.5. More preferably, the value of x is from 0.01 to 0.125. The molar ratio of silicon to titanium in the lattice framework of the zeolite is advantageously from 9.5:1 to 99:1 (most preferably from 9.5:1 to 60:1). The use of relatively titanium-rich zeolites may also be desirable. Particularly preferred titanium zeolites include the class of molecular sieves commonly known as titanium silicalites (see *Catal. Rev.-Sci. Eng.* 39(3) (1997) 209). Examples of these include TS-1, TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, ZSM-12, MCM-22, MCM-41, and MCM-48 are also suitable for use. Examples of MCM-22, MCM-41, and MCM-48 zeolites are described in U.S. Pat. Nos. 4,954,325, 6,077,498, and 6,114,551; Maschmeyer, T., et al, *Nature* 378(9) (1995) 159; Tanev, P. T., et al., *Nature* 368 (1994) 321; Corma, A., *J. Chem. Soc., Chem. Commun.* (1998) 579; Wei D., et al., *Catal. Today* 51 (1999) 501). The most preferred is TS-1.

Suitable noble metals include, e.g., gold, silver, platinum, palladium, iridium, ruthenium, rhenium, rhodium, osmium, and mixtures thereof. Preferred noble metals are Pd, Pt, Au, Re, Ag, and mixtures thereof. A catalyst comprising palladium is particularly preferred. Typically, the amount of noble metal present in the catalyst is in the range of from 0.01 to 20 wt %, preferably from 0.1 to 5 wt %.

The noble metal and the transition metal zeolite may be on a single particle or on separate ones. For example, the noble metal may be supported on the transition metal zeolite. Alternatively, the catalyst may comprise a mixture of a transition metal zeolite and a noble metal supported on a carrier. Suitable carriers for the supported noble metal include carbons, titanias, zirconias, niobias, silicas, aluminas, silica-aluminas, titania-silicas, ion-exchange resins, and the like, and mixtures thereof.

The manner in which the noble metal is incorporated into the catalyst is not critical. For example, the noble metal may be supported on the transition metal zeolite or other carriers by impregnation, ion exchange, adsorption, precipitation, or the like.

The weight ratio of the transition metal zeolite to the noble metal is not particularly critical. However, a transition metal zeolite to noble metal weight ratio of from 10:1 to 10,000:1 is preferred.

The catalyst may be a powder or particles of various shapes and sizes. Suitable catalysts have a particle size in the range of about 0.0001 to about 3 mm. The catalyst may be formed into particles by pelletization, spray-drying, extrusion, and the like.

The process uses propylene. Any gas comprising propylene may be used. Typically, it comprises greater than 90 wt % propylene. Preferably, it comprises greater than 95 wt % propylene. A mixture of propylene and propane may be used.

The process uses oxygen. Any gas comprising oxygen may be used. Typically, it comprises greater than 10 wt % oxygen. Preferably, it comprises greater than 90 wt % oxygen.

The process uses hydrogen. Any gas comprising hydrogen may be used. Typically, it comprises greater than 10 wt % hydrogen. Preferably, it comprises greater than 90 wt % hydrogen.

The molar ratio of hydrogen to oxygen can usually be varied in the range of 1:100 to 10:1 and is especially favorable at 1:5 to 2:1. The molar ratio of oxygen to propylene is usually 1:1 to 1:20, and preferably 1:1.5 to 1:10.

In addition to propylene, oxygen, and hydrogen, a diluent gas may be used. Suitable diluent gases include nitrogen, helium, argon, carbon dioxide, and saturated hydrocarbons (e.g., methane, ethane, propane, and n-butane). Mixtures of those diluent gases can be used. The molar ratio of propylene to diluent gas is usually in the range of 100:1 to 1:20, especially 20:1 to 1:20.

The process uses a solvent. Suitable solvents are liquid under the reaction conditions. They include, for example, oxygen-containing hydrocarbons such as alcohols, aromatic and aliphatic solvents such as toluene and hexane, nitriles such as acetonitrile, and water. Suitable oxygenated solvents include alcohols, ethers, esters, ketones, water, and the like, and mixtures thereof. Preferred oxygenated solvents include water, methanol, ethanol, isopropanol, tert-butanol, and mixtures thereof. Particularly preferred oxygenated solvents are selected from the group consisting of water, methanol, and mixtures thereof.

The process uses a buffer. The buffer is employed in the reaction to inhibit the formation of propylene glycols or glycol ethers during the epoxidation, and it can improve the reaction rate and selectivities. The buffer is typically added to the solvent to form a buffer solution, or the solvent and the buffer are added separately. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkylammoniums, pyridiniums), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. More preferred buffers include alkali metal phosphates and ammonium phosphates. The ammonium phosphates buffer is particularly preferred. For example, a buffer comprising an ammonium ion and phosphate ion in a molar ratio of 1:1 to 3:1 may be used.

The reaction step is typically performed at a temperature in the range of from 30 to 100° C., preferably in the range of from 50 to 70° C., and at a pressure in the range of from 100 to 800 psig, preferably in the range of from 150 to 400 psig.

The catalyst is preferably in the form of a suspension or a fixed bed. The process may be performed in a continuous-flow, semi-batch, or batch mode. A continuous-flow process is preferred.

The reaction step produces a reaction mixture comprising propylene, propylene oxide, hydrogen, oxygen, solvent, buffer, and other byproducts.

The process comprises separating light components (e.g., propylene, propane, propylene oxide, hydrogen, oxygen, solvent(s), and diluent gas if used) from the reaction mixture to produce a heavy residue comprising the buffer. Typically, the heavy residue comprises water and organic compounds such as propylene glycol and propylene glycol ethers. Many different methods may be used for the separation. For example, the separation may include a distillation step to recover the solvent and an evaporation step to further concentrate the heavy residue. As an example, the process is illustrated in FIG. 1, where a mixture of water and methanol is used as the solvent for the epoxidation of propylene. A feed comprising propylene, oxygen, hydrogen, methanol, water, and a buffer solution is fed to reactor 101 and reacted in the presence of a catalyst to produce a reaction mixture. The reaction mixture is passed via line 2 to flash separator 102 wherein vapor and liquid phases are separated. The vapor fraction is passed via line 3 to propylene oxide absorber 103 wherein propylene oxide in the vapor is absorbed with a methanol-water mixture fed via line 6 to the absorber. Overhead vapors from absorber 103, except for a small purge, are recycled via line 5 to reactor 101. The liquid stream from flash separator 102 and the liquid stream at the bottom of propylene oxide absorber 103 are passed respectively via lines 4 and 7 to low-pressure depropanizer 104. The depropanized liquid at the bottom of depropanizer 104 is fed via line 9 to crude propylene oxide column 105, wherein crude propylene oxide is distilled as overhead via line 10 for further purification. The bottoms stream 11 is fed to methanol recovery column 106. The distilled methanol is recovered as overhead via line 12. The bottoms stream from methanol column 106 comprises mostly water, propylene glycol, propylene glycol ethers, and buffer. Typically, it comprises from 60 to 85 wt % water, from 0.5 wt % to 5 wt % buffer, and from 10 to 30 wt % organic components. The bottoms stream may be further concentrated in an evaporator. Standard evaporators may be used, see Robert H. Perry and Don W. Green, *Perry's Chemical Engineers' Handbook*, Seventh Edition, McGraw Hill (1997) pp. 11-107 to 11-114. Preferably, a multi-effect evaporator is used. A heavy residue comprising the buffer is produced following evaporation. Typically, the heavy residue comprises from 2 wt % to 50 wt % buffer.

The process comprises adding a precipitating agent to the heavy residue to form a mixture of buffer precipitates and a mother liquor. Addition of a precipitating agent in the heavy residue lowers the solubility of the buffer in the resulting liquid, precipitating the solid buffer. The precipitating agent may be any organic solvent that can cause the precipitation of the buffer from the heavy residue. Typically, the buffer has a solubility of less than 0.1 g per 100 g in the precipitating agent, preferably the solubility is less than 0.01 g per 100 g. Suitable precipitating agents include ethers, alcohols, esters, ketones, and the like. The preferred precipitating agent is selected from the group consisting of methanol, propylene oxide, acetone, and mixtures thereof. Methanol is particularly preferred.

The process comprises separating the buffer precipitates from the mother liquor. Conveniently, a crystallizer is used for the precipitation and separation of the buffer from the mother liquor. The crystallizer is preferably operated at a temperature in the range of −10 to 25° C., more preferably at 0 to 10° C., and at atmospheric pressure. The volume ratio of the precipitating agent to the heavy residue may be from 1:1 to 10:1, preferably from 2:1 to 5:1 to improve the buffer recovery. The buffer precipitates can be isolated from the mother liquor by settling, filtration, centrifugation, or their combinations. Filtration is preferably used. Conveniently, the buffer collected from the crystallizer is recycled to reactor 101. The mother liquor is preferably processed to recover the precipitating agent; the recovered precipitating agent is preferably recycled to the crystallizer.

An example of buffer precipitation and precipitating agent recovery is illustrated in FIG. 1. The heavy residue is passed to the crystallizer 108 via line 15. The crystallizer overflow solution (mother liquor) is fed to precipitating agent recovery column 109 to separate the precipitating agent from a bottoms stream containing water and other heavy organic components. The bottoms stream exits the column via line 19. The buffer precipitates are recycled to reactor 101. Conveniently, buffer precipitates are dissolved in a make-up buffer solution or water and fed to the reactor.

Example

Propylene Oxide Production

The following is one proposed method of practicing the process of the invention.

A catalyst is prepared by following the procedure taught by Example 5 of the copending application Ser. No. 11/891,460, filed on Aug. 10, 2007. Propylene, hydrogen, oxygen, nitrogen, methanol, water, and an ammonium phosphate buffer solution are fed to an epoxidation reactor 101. The reaction is operated at 60° C. and under pressure of 300 psig.

The reaction mixture containing 1.6 wt % propylene, 0.7 wt % propane, 4.8 wt % propylene oxide, 0.04 wt % hydrogen, 0.7 wt % oxygen, 62 wt % methanol, 22 wt % water, 0.11 wt % ammonium phosphate, and nitrogen diluent gas is passed to flash separator 102. The liquid stream from flash separator 102 comprises 5.2 wt % propylene oxide, 0.5 wt % propylene, 0.2 wt % propane, 68 wt % methanol, 24 wt % water, and 0.12 wt % ammonium phosphate. The vapor stream comprising 0.41 mole percent (mol %) propylene oxide, 3.5 mol % propane, 6.7 mol % oxygen, 5.3 mol % hydrogen, and nitrogen is passed via line 3 to propylene oxide absorber 103 wherein propylene oxide is absorbed into a methanol-water mixture. The absorber 103 has about 20 theoretical stages. The recycle solvent (obtained as overhead of solvent recovery column 106) is chilled to 15° C. and fed to the top of the absorber 103 at a flow rate of 6 kg/h via line 6. The absorber exit gas (containing primarily propylene, propane, oxygen, hydrogen, and nitrogen), after a small purge, is recompressed (not shown) and recycled to the reactor via line 5. Both the absorber bottom liquid effluent (via line 7) and the separator liquid product (via line 4) are fed to depropanizer 104. The depropanizer 104 has 20 theoretical stages. Its overhead temperature is 3° C. and pressure is 10 psig. Its bottom temperature is 82° C. and pressure is 10.2 psig. A C3 stream, comprising mostly propylene and propane exiting the depropanizer 104 via line 8, is sent to a C3 splitter (a distillation column, not shown) for propylene enrichment (or partial propane removal) before it is recycled to reactor 101. The depropanizer liquid stream 9 is fed to crude propylene oxide column 105. The crude propylene oxide column 105 has 44 theoretical stages. Its overhead temperature is 36° C. and pressure is 1.0 psig. Its bottom temperature is 75° C. and pressure is 1.4 psig. Crude propylene oxide is obtained as an overhead distillate via line 10, and further purified to produce commercial grade propylene oxide (not shown). The bottoms stream, comprising 70 wt % methanol, 26 wt % water, propylene oxide derivatives (e.g., propylene glycol, propylene glycol monomethyl ethers, dipropylene glycol, and dipropylene glycol methyl ethers), and ammonium phosphate, exits column 105 via line 11 and enters solvent recovery column 106. Column 106 has 16 theoretical stages. Its overhead temperature is 74° C. and pressure is about 0 psig. Its bottom temperature is 100.5° C. and pressure is 0.20 psig. A methanol-containing solvent is recovered as overhead and is recycled to the reactor 101 via line 12. The bottoms stream of the solvent-recovery column, comprising 12 wt % propylene glycol monomethyl ethers, 2 wt % propylene glycol, 0.5 wt % heavy glycol and glycol ethers, 1.8 wt % ammonium phosphates, and 83% water, is removed via line 13 and fed to a 5-stage multi-effect evaporator 107. The condensates from the $2^{nd}$-effect to $5^{th}$-effect stage evaporators are sent via line 14 for glycol ether recovery and waste water treatment. The heavy residue comprising 8 wt % propylene glycol ethers, 5 wt % other heavy organics, 3.6 wt % ammonium phosphates, and 83 wt % water, is mixed with chilled methanol at 0° C. from line 18 at 1:8 volume ratio in crystallizer 108. The precipitated buffer is passed via line 17 and mixed with a make-up ammonium phosphate solution in line 20. The mixed buffer solution is recycled to reactor 101. The mother liquor is drawn off via line 16 and fed to precipitating agent recovery column 109 for methanol recovery. The bottoms stream containing water and heavy organics is disposed of via line 19.

I claim:
1. A process for producing propylene oxide comprising
    (a) reading propylene, oxygen, and hydrogen in the presence of a catalyst, a solvent, and a buffer to produce a reaction mixture comprising propylene oxide;
    (b) separating light components from the reaction mixture to produce a heavy residue comprising the buffer;
    (c) adding a precipitating agent in the heavy residue to form a mixture of buffer precipitates and a mother liquor; and
    (d) separating the buffer precipitates from the mother liquor;
wherein the step (c) is operated at a temperature in the range of −10 to 25° C.
2. The process of claim 1 wherein the buffer precipitates are recycled to the reaction step.
3. The process of claim 1 further comprising separating the precipitating agent from the mother liquor and recycling the separated precipitating agent to step (c).
4. The process of claim 1 wherein step (b) comprises a distillation step to recover the solvent and an evaporation step to concentrate the heavy residue.
5. The process of claim 4 wherein the evaporation is performed by a multi-effect evaporator.
6. The process of claim 1 wherein the buffer precipitates are separated from the mother liquor by filtration.
7. The process of claim 1 wherein the buffer has a solubility of less than 0.1 g per 100 g in the precipitating agent.
8. The process of claim 1 wherein the buffer has a solubility of less than 0.01 g per 100 g in the precipitating agent.
9. The process of claim 1 wherein the buffer comprises an ammonium ion and a phosphate ion in a molar ratio of from 1:1 to 3:1.
10. The process of claim 1 wherein the precipitating agent is selected from the group consisting of propylene oxide, methanol, acetone, and mixtures thereof.
11. The process of claim 1 wherein the precipitating agent is methanol.
12. The process of claim 1 wherein step (c) is operated at a temperature in the range of 0 to 10° C.
13. The process of claim 1 wherein the catalyst comprises a transition metal zeolite and a noble metal.
14. The process of claim 1 wherein the solvent is selected from the group consisting of methanol, water, and mixtures thereof.

* * * * *